United States Patent
Reed

(10) Patent No.: US 9,834,614 B2
(45) Date of Patent: *Dec. 5, 2017

(54) METHOD OF INCREASING PLASMIN ACTIVITY THROUGH ANTIPLASMIN CONVERSION

(71) Applicant: Translational Sciences Inc., Memphis, TN (US)

(72) Inventor: Guy L. Reed, Memphi, TN (US)

(73) Assignee: Translational Sciences Inc., Memphis, TN (US)

( * ) Notice: Subject to any disclaimer, the term of this patent is extended or adjusted under 35 U.S.C. 154(b) by 50 days.

This patent is subject to a terminal disclaimer.

(21) Appl. No.: 14/872,776

(22) Filed: Oct. 1, 2015

(65) Prior Publication Data

US 2016/0039943 A1 Feb. 11, 2016

Related U.S. Application Data

(63) Continuation of application No. 12/597,311, filed as application No. PCT/US2008/061662 on Apr. 25, 2008, now Pat. No. 9,150,903.

(60) Provisional application No. 60/913,913, filed on Apr. 25, 2007.

(51) Int. Cl.
| | |
|---|---|
| *C07K 16/38* | (2006.01) |
| *C12Q 1/56* | (2006.01) |
| *G01N 33/86* | (2006.01) |
| *A61K 39/395* | (2006.01) |
| *A61K 39/00* | (2006.01) |

(52) U.S. Cl.
CPC .......... *C07K 16/38* (2013.01); *A61K 39/3955* (2013.01); *C12Q 1/56* (2013.01); *G01N 33/86* (2013.01); *A61K 2039/505* (2013.01)

(58) Field of Classification Search
CPC .................................................... C07K 16/38
See application file for complete search history.

(56) References Cited

U.S. PATENT DOCUMENTS

| | | | |
|---|---|---|---|
| 6,114,506 A | 9/2000 | Reed et al. | |
| 7,309,774 B2 | 12/2007 | McKee et al. | |
| 9,150,903 B2* | 10/2015 | Reed | C12Q 1/56 |
| 2002/0086025 A1* | 7/2002 | Reed | A61K 38/49 424/184.1 |
| 2003/0017147 A1* | 1/2003 | Reed | A61K 39/395 424/130.1 |
| 2003/0031664 A1* | 2/2003 | Reed | A61K 39/395 424/131.1 |

FOREIGN PATENT DOCUMENTS

| | | |
|---|---|---|
| EP | 0272609 A2 | 6/1988 |
| WO | 99/61072 A2 | 12/1999 |
| WO | 2004/042000 | 5/2004 |
| WO | 2006/005583 | 1/2006 |

OTHER PUBLICATIONS

Reed et al., 1990, Inhibition of Clot-Bound _2-Antiplasmin Enhances In Vivo Thrombolysis, Circulation, 82: 1: 164-168.*
Mimuro et al., 1987, Monoclonal Antibodies to Discrete Regions in _2-Plasmin Inhibitor, Blood, 2: 446-453.*
Anonick et al., 1991, "Soluble Fibrin Preparations Inhibit the Reaction of Plasmin with Alpha-2-Macroglobulin: Comparison with Alpha-2-Antiplasmin and Leupeptin," Biochem. J., vol. 275, pp. 53-59.
Holmes et al., 1987, "Characterization of Recombinant Human cu2-Antiplasmin and of Mutants Obtained by Site-Directed Mutagenesis of the Reactive Site," Biochemistry, vol. 26, p. 5133.
Potempa et al., 1988, "Alpha-2-Antiplasmin: A Serpin with Two Separate but Overlapping Reactive Sites," Science, vol. 241, No. 4866, pp. 699-700 (abstract only).
International Search Report for PCT/US08/061662 dated Aug. 18, 2008 (1 page).
Sazonova et al., 2007, "Fibrinolysis is Amplified by Converting alpha 2-Antiplasmin from a Plasmin Inhibitor to a Substrate," Journal of Thrombosis and Haemostasis, 5:2087-2904.

* cited by examiner

*Primary Examiner* — Amber D Steele
(74) *Attorney, Agent, or Firm* — Eversheds Sutherland (US) LLP

(57) ABSTRACT

Methods for increasing plasmin activity in a patient in need thereof are provided, comprising administering to the patient a therapeutic amount of an agent which binds to α2-antiplasmin at a binding site to increase conversion of α2-antiplasmin from an inhibitor to a plasmin substrate, thereby increasing plasmin activity in the patient. Also provided are methods for the identification of compounds or molecules that increase plasmin activity, comprising determining whether the compound or molecule binds to a binding site on α2-antiplasmin which increases the conversion of α2-antiplasmin from an inhibitor to a plasmin substrate, wherein the compound or molecule is not an antibody, thereby identifying a compound or molecule which increases plasmin activity. Further provided are pharmaceutical compositions and methods of use thereof for the treatment of myocardial infarction, thrombosis, ischemic stroke, and pulmonary embolism.

25 Claims, 8 Drawing Sheets

FIG. 4 – Cont.
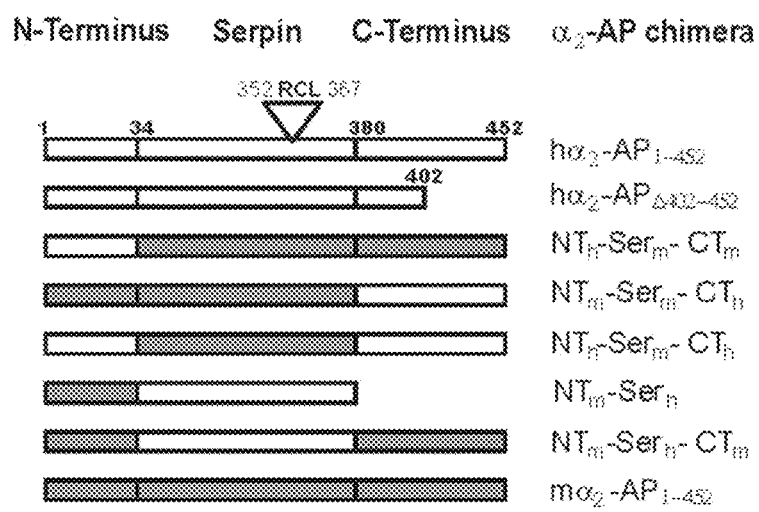
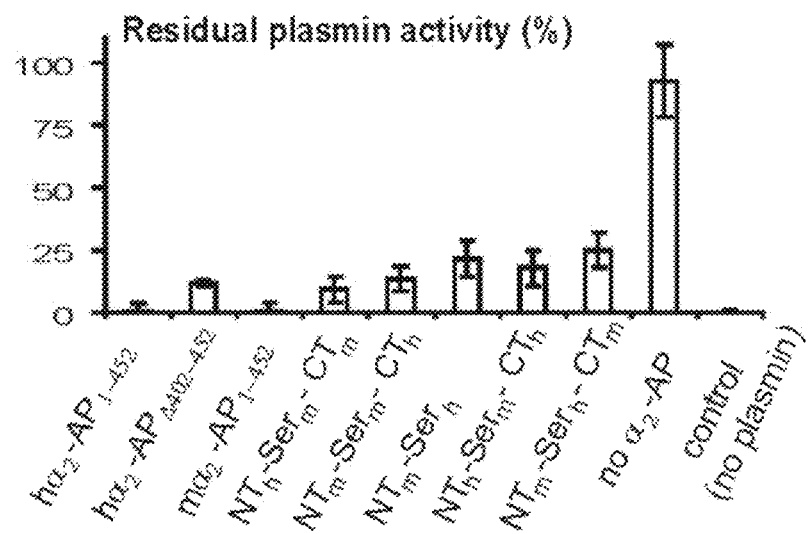

FIG. 4 – Cont.
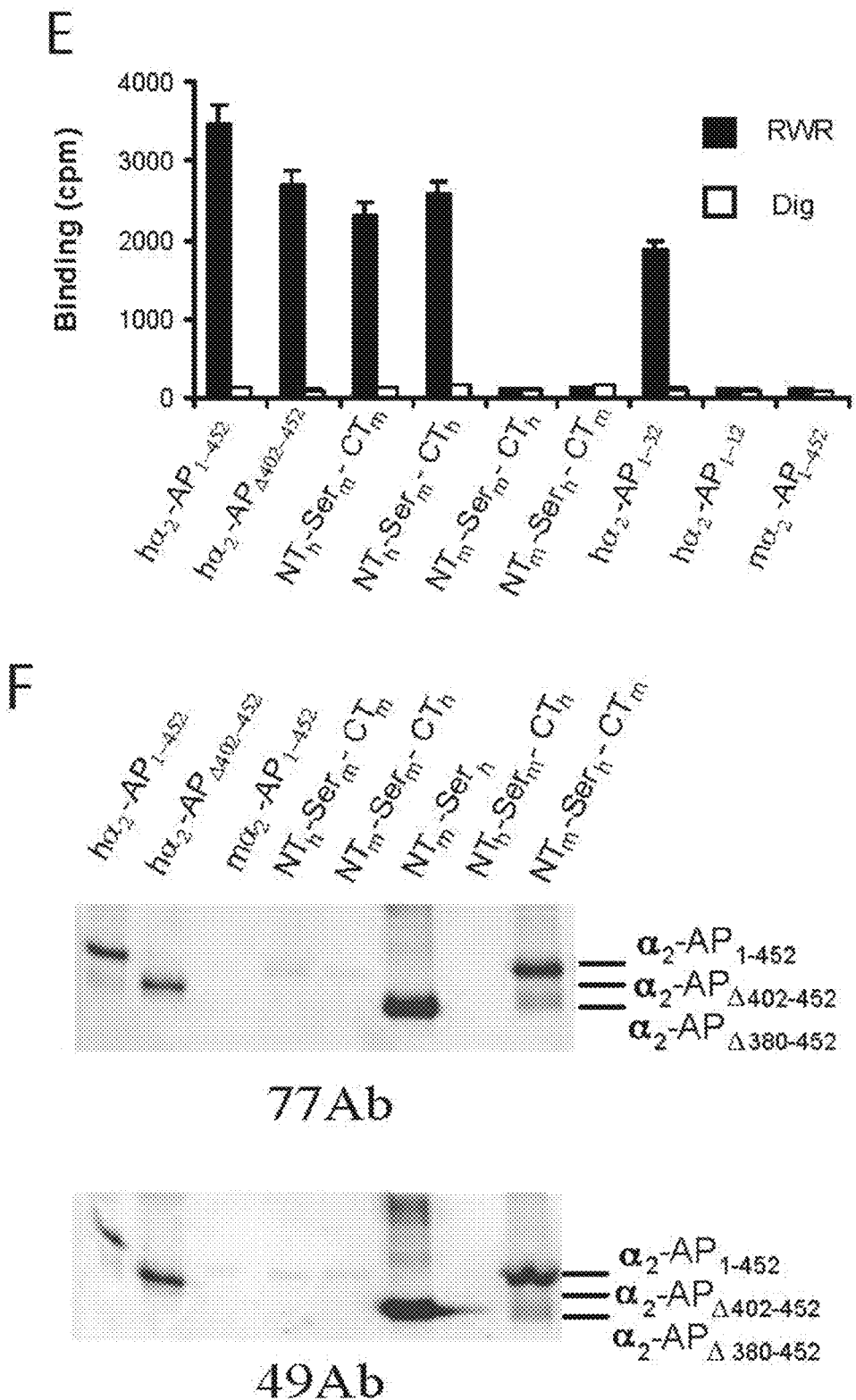

| α₂-AP chimera | MAb | | | |
|---|---|---|---|---|
| | 49 | 77 | RWR | Dig (control) |
| hα₂-AP$_{1-452}$ | + | + | + | − |
| hα₂-AP$_{Δ402-452}$ | + | + | + | − |
| NT$_h$-Ser$_m$-CT$_m$ | − | − | + | − |
| NT$_m$-Ser$_m$-CT$_h$ | − | − | − | − |
| NT$_h$-Ser$_m$-CT$_h$ | − | − | + | − |
| NT$_m$-Ser$_h$ | + | + | − | − |
| NT$_m$-Ser$_h$-CT$_m$ | + | + | − | − |
| mα₂-AP$_{1-452}$ | − | − | − | − |

SEQUENCE LISTING

<160> NUMBER OF SEQ ID NOS: 19

<210> SEQ ID NO 1
<211> LENGTH: 20
<212> TYPE: PRT
<213> ORGANISM: Homo sapiens

<400> SEQUENCE: 1

Leu Gly Asn Gln Glu Pro Gly Gly Gln Thr Ala Leu Lys Ser Pro Pro
 1               5                  10                  15

Gly Val Cys Ser
            20

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcatatggc ccagcagaag ctg                                          23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcgagctgg cagggagga c                                             21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtcatatgaa ccaggagcag gtg                                          23

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtctcctctg cagttgggtc tctgctgcag actcc                             35

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

-continued gtcatatggc ccagcagaag ctg                                              23

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tctgctctgg agttgggaca ctctt                                            25

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aactccagag cagacccac                                                   19

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ttataaagaa gaggaagggg cg                                               22

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccaactgcag aggagac                                                     17

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctgtggtgt cctcgaagat gaagaagagg aaggg                                 35

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcgaggaca ccacaggc                                                    18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcctcgagg agccgtgg                                                 18

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgccccttcc tcttctttat aa                                            22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctcgagctgg caggggagga c                                             21

<210> SEQ ID NO 16
<211> LENGTH: 14
<212> TYPE: PRT
<213> ORGANISM: Homo sapiens

<400> SEQUENCE: 16

Asn Gln Glu Gln Val Ser Pro Leu Thr Leu Leu Lys Leu Gly
  1               5                  10

<210> SEQ ID NO 17
<211> LENGTH: 26
<212> TYPE: PRT
<213> ORGANISM: Homo sapiens

<400> SEQUENCE: 17

Gly Asp Lys Leu Phe Gly Pro Asp Leu Lys Leu Val Pro Pro Met Glu
  1               5                  10                  15

Glu Asp Tyr Pro Gln Phe Gly Ser Pro Lys
             20                  25

<210> SEQ ID NO 18
<211> LENGTH: 32
<212> TYPE: PRT
<213> ORGANISM: Homo sapiens

<400> SEQUENCE: 18

Asn Gln Glu Gln Val Ser Pro Leu Thr Leu Leu Lys Leu Gly Asn Gln
  1               5                  10                  15

Glu Pro Gly Gly Gln Thr Ala Lys Leu Ser Pro Pro Gly Val Cys Ser
             20                  25                  30

```
<210> SEQ ID NO 19
<211> LENGTH: 12
<212> TYPE: PRT
<213> ORGANISM: Homo sapiens

<400> SEQUENCE: 19

Asn Gln Glu Gln Val Ser Pro Leu Thr Leu Leu Lys
 1               5                  10
```

METHOD OF INCREASING PLASMIN ACTIVITY THROUGH ANTIPLASMIN CONVERSION

CROSS REFERENCE TO RELATED APPLICATIONS

This application is a continuation of U.S. application Ser. No. 12/597,311 filed Oct. 23, 2009, allowed, which is claims priority to PCT Application No. PCT/US2008/061662 filed Apr. 25, 2008, which claims priority to U.S. Provisional Application No. 60/913,913 filed Apr. 25, 2007, the entire contents of which are hereby incorporated by reference in their entirety.

ACKNOWLEDGEMENT OF FEDERAL RESEARCH SUPPORT

This invention was made, in part, with Government support under National Institutes of Health Grant HL-058496 to G.L.R. Accordingly, the United States Government has certain rights in this invention.

FIELD OF THE INVENTION

This invention relates generally to compositions and methods for improving the healing of tissue (e.g., wounds, liver, vessels), modifying angiogenesis (e.g., in conditions such as eye disease, cancer, ischemia), or treating stroke or thrombotic diseases (e.g., heart attacks, venous thrombosis, pulmonary embolism, shunt thrombosis). In particular, therapeutic agents are provided which increase plasmin activity by increasing the conversion of α2-antiplasmin from a plasmin inhibitor to a plasmin substrate.

BACKGROUND

Acute myocardial infarction, ischemic stroke, and peripheral arterial disease are caused by thrombotic occlusion of blood vessels by fibrin-containing thrombi. Enzymatic dissolution of these thrombi (fibrinolysis) by plasmin, a serine protease, reduces death and disability. Fibrinolysis is initiated by plasminogen activators that cleave the proenzyme plasminogen to plasmin (Collen et al., 1991, *Blood* 78: 3114-3124). Fibrinolysis is also under the control of regulatory molecules such as $\alpha_2$-antiplasmin ($\alpha_2$-AP), factor XIII, thrombin, plasminogen activator inhibitor-1 (PAI-1), and thrombin-activatable fibrinolysis inhibitor (Collen et al., 1991, *Blood* 78: 3114-3124; Tsikouris et al., 2002, *J Clin Pharmacol* 42:1187-1199; Lee et al., 2000, *J Biol Chem* 275: 37382-37389; Bajzar et al., 2000, *Arterioscler Thromb Vasc Biol* 20: 2511-2518). Plasmin is released as plasminogen into the circulation and is activated by tissue plasminogen activator (tPA), urokinase plasminogen activator (uPA), thrombin, fibrin, and factor XII (Hageman factor). Plasmin is inactivated by α2-antiplasmin, a serine protease inhibitor (serpin). Apart from fibrinolysis, plasmin also proteolyses proteins in various other systems, including but not limited to, fibrin, fibronectin, thrombospondin, laminin, and von Willebrand factor.

Plasmin is known to have a central role in degrading fibrin, the protein component of blood clots. More recently it has been recognized that plasmin activity is important for degrading protein matrices as well as modifying the activity of enzymes and growth factors. Plasmin affects vessel remodeling, cell migration, wound and organ healing, growth factor function, angiogenesis, tumor growth and dissemination, and infection (Li et al., 2003, *Wound Repair Regen.* 11(4):239-247; Castellino et al., 2005, *Thromb Haemost.* 93(4):647-654; Rakic et al., 2003, *Cell Mol Life Sci.* March 60(3):463-473; Kramer et al., 1994, *Invasion Metastasis.* 14(1-6):210-222).

Among the plasmin inhibitory molecules, $\alpha_2$-AP may be the most important fibrinolytic regulator in the formed thrombus (van Giezen et al., 1992, *Blood Coagul Fibrinolysis* 4:869-875; Butte et al., 1997, *Circulation* 95: 1886-1891; Nagai et al., 2001, *Blood* 97: 3086-3092). $\alpha_2$-AP is a single chain glycoprotein (70 kDa) that belongs to the serine protease inhibitor (serpin) family (Holmes et al., 1987, *J Biol Chem* 1987; 262: 1659-1664). $\alpha_2$-AP has an N-terminal domain which binds fibrin, a C-terminal domain which binds plasmin kringles, and a serpin domain which contains the reactive center loop (RCL) with the scissile P1-P1' reactive bond that reacts with the active site of plasmin. It has been proposed that serpins inhibit their target proteases through a multiple step reaction that involves the formation of a serpin-protease Michaelis complex, followed by the formation of a serpin-acyl-protease intermediate which then proceeds to the inhibitory pathway (with distortion and inactivation of the protease) or to the substrate pathway (with deacylation and cleavage of the serpin by the protease) (Huntington et al., 2000, *Nature* 407:923-926; Wiman and Collen, 1978, *Eur J Biochem* 84:573-578; Schechter and Plotnick, 2004, *Methods* 32:159-168). $\alpha_2$-AP inhibits plasmin in one of the fastest protein-protein reactions described, and plasmin-$\alpha_2$-AP interactions appear to proceed predominantly through the inhibitory pathway (Wiman and Collen, 1978, *Eur J Biochem* 84:573-578). Indeed $\alpha_2$-AP is such a potent inhibitor that the half-life of plasmin in vivo is thought to be less than 100 msec (Edy and Collen, 1977, *Biochim Biophys Acta* 484:423-432). One strategy for amplifying fibrinolysis is to block the inhibitory effects of $\alpha_2$-AP. Inhibition of $\alpha_2$-AP by monoclonal antibodies (MAbs) causes "spontaneous" lysis of blood clots in the absence of exogenous plasminogen activator (Reed et al., 1988, *Trans Assoc Am Physicians* 101:250-256) and synergistically amplifies fibrinolysis by all plasminogen activators in vitro and in vivo (Reed, 1997, *Hybridoma* 16:281-286).

What is needed are additional compositions and methods for improving the healing of tissue (e.g., wounds, liver, vessels), modifying angiogenesis (e.g., in conditions such as eye disease, cancer, ischemia), or treating stroke or thrombotic diseases (e.g., heart attacks, venous thrombosis, pulmonary embolism, shunt thrombosis). In particular, it would be desirable to determine the mechanisms through which currently available inhibitors of $\alpha_2$-AP affect the activity of plasmin and regulate fibrinolysis. It also would be desirable to provide methods for screening for additional molecules and compounds that can increase plasmin activity in a patient in need thereof.

SUMMARY OF THE INVENTION

Methods of increasing plasmin activity in a patient in need thereof are provided, comprising administering to the patient a therapeutic amount of an agent which binds to α2-antiplasmin at a binding site to increase conversion of α2-antiplasmin from an inhibitor to a plasmin substrate, thereby increasing plasmin activity in the patient. In certain embodiments, the methods are used for improving the healing of tissue (e.g., wounds, liver, vessels), modifying angiogenesis (e.g., in conditions such as eye disease, cancer, ischemia), or treating stroke or thrombotic diseases (e.g., heart attacks, venous thrombosis, pulmonary embolism, shunt thrombosis). In one embodiment, the method increases fibrinolysis. In some embodiments, the binding agent is an antibody or antibody fragment. In some embodiments, the binding agent is specifically not an antibody or antibody fragment.

In certain embodiments, the binding site comprises a serpin domain which is not a reactive center loop. In other embodiments, the binding site comprises a portion of the amino-terminus of α2-antiplasmin. In certain of those embodiments, the binding site has an amino acid sequence of LGNQEPGGQTALKSPPGVCS (SEQ ID NO:1). In other embodiments, the binding site is adjacent to the site at which α2-antiplasmin cross-links to fibrin. The methods of increasing plasmin activity are useful in a number of situations, for example, for increasing fibrinolysis and/or for modulating angiogenesis, vascular remodeling, and/or malignancies. The methods of increasing fibrinolysis are useful, for example, in a patient that has a disease or condition selected from the group consisting of myocardial infarction, thrombosis, ischemic stroke, and pulmonary embolism. In some embodiments, the methods further comprise administering to the patient an agent that facilitates the degradation of fibrin, that prevents fibrin formation, or that interferes with platelet formation. In certain embodiments, the agent is selected from the group consisting of plasmin, staphylokinase, streptokinase, prourokinase, urokinase, tissue-type plasminogen activator, vampire bat plasminogen activator, heparin, hirudin, activated protein C, ticlopidine, aspirin, clopidigrel, and an inhibitor of glycoprotein IIb/IIIa function.

Additional methods are provided for screening for a compound or molecule which increases plasmin activity, comprising determining whether a compound or molecule binds to a binding site on α2-antiplasmin which increases the conversion of α2-antiplasmin from a plasmin inhibitor to a plasmin substrate, thereby identifying a compound or molecule which increases plasmin activity. In certain embodiments, the binding site comprises a serpin domain which is not a reactive center loop. In some of those embodiments, the compound or molecule is an antibody or antibody fragment. In other embodiments, the binding site comprises a portion of the amino-terminus of α2-antiplasmin. In certain of those embodiments, the binding site has an amino acid sequence of LGNQEPGGQTALKSPPGVCS (SEQ ID NO:1). In other embodiments, the binding site is adjacent to the site at which α2-antiplasmin cross-links to fibrin. The binding of the compound or molecule to the binding site on α2-antiplasmin is determined, in some instances, by a standard binding assay. In one embodiment, the binding is performed by phage display technology.

Pharmaceutical compositions are provided that comprise an effective amount of a compound or molecule used in the disclosed methods for increasing plasmin activity or identified by the disclosed methods for identifying a compound or molecule that increases plasmin activity. These pharmaceutical compositions are useful, for example, for increasing fibrinolysis and/or for modulating angiogenesis, vascular remodeling, and/or malignancies. The methods of increasing fibrinolysis are useful, for example, in a patient that has a disease or condition selected from the group consisting of myocardial infarction, thrombosis, ischemic stroke, and pulmonary embolism.

DETAILED DESCRIPTION OF THE INVENTION

Figure 1:
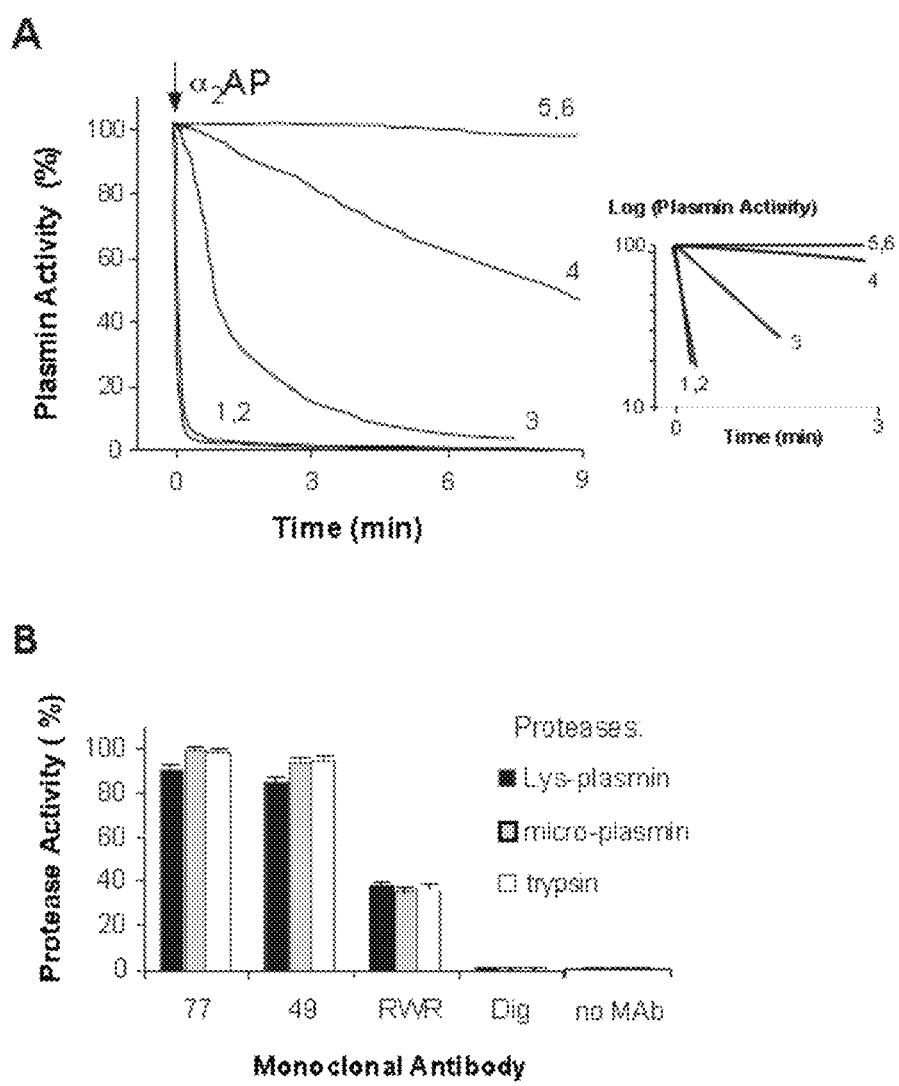
FIG. 1 shows the influence of MAbs on the inhibition of various serine proteases by $\alpha_2$-AP. Panel A is a graph showing the effect of MAbs on the rate of plasmin inhibition. Plasmin (20 nM) was added to a cuvette containing S2251 (500 µM) in TBS buffer. Plasmin amidolytic activity was continuously monitored at 405 nm prior to and after the addition of native human $\alpha_2$-AP (60 nM) that was pre-incubated with no MAb (curve 1), Dig (control) MAb (60 nM; curve 2), MAb RWR (60 nM; curve 3 or 600 nM; curve 4), MAb 77 (60 nM; curve 5) or MAb 49 (60 nM; curve 6) as described in Materials and Methods. Inset, same data shown in log transformation. Panel B is a bar graph showing the effect of MAbs on inhibition of archetypal serine proteases by $\alpha_2$-AP. Plasmin, micro-plasmin or trypsin (20 nM) was added to a cuvette containing TBS buffer with native $\alpha_2$-AP (60 nM) that was pre-incubated with MAbs (600 nM RWR; 60 nM 49, 77 and Dig). After 10 minutes, additional incubation at 37° C. the residual protease activity was determined. The initial value of activity was defined as 100%.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

It must be noted that as used herein and in the appended claims, the singular forms "a," "an," and "the," include plural forms unless the context clearly indicates otherwise. Thus, for example, reference to "an agent" includes one or more of such different agents, and reference to "the method" includes reference to equivalent steps and methods known to those of ordinary skill in the art that could be modified or substituted for the methods described herein.

Unless otherwise defined, all technical and scientific terms used herein have the meaning as commonly understood by one of ordinary skill in the art to which this invention belongs. The practice of the present invention employs, unless otherwise indicated, conventional techniques of cell biology, molecular biology, genetics, chemistry, microbiology, recombinant DNA, and immunology. See, for example, Maniatis et al. (1982) Molecular Cloning, A Laboratory Manual, latest edition, Cold Spring Harbor Laboratory, Cold Spring Harbor, N.Y.; Sambrook et al. (1989) Molecular Cloning: A Laboratory Manual, latest edition (Cold Spring Harbor, N.Y.: Cold Spring Harbor Laboratory Press); Ausubel et al. (1992) Current Protocols in Molecular Biology, latest edition (New York: John Wiley & Sons); Guthrie & Fink (1991) Methods Enzymol. 194:1-863; Cell Biology, A Laboratory Manual, ed. Celis, J. E., Academic Press, NY; Histochemistry, Pearse, A. G. E., Vol. 1 (1980), Vol. 2 (1985), and Vol. 3 (1990).

The present disclosure describes for the first time that certain monoclonal antibodies used to increase plasmin activity act by binding to different structural elements of $\alpha_2$-AP that convert α2-AP from a plasmin inhibitor to a plasmin substrate. Accordingly, methods of increasing plasmin activity in a patient in need thereof are provided, comprising administering to the patient a therapeutic amount of an agent which binds to α2-antiplasmin at a binding site to increase conversion of α2-antiplasmin from an inhibitor to a plasmin substrate, thereby increasing plasmin activity in the patient. Also provided in the present invention are α2-AP binding agents or molecules which are specifically not antibodies or fragments thereof. In certain embodiments, the binding agent or molecule is a nucleic acid, receptor decoy, ribozyme, sense polynucleotide, double stranded RNA, RNAi, aptamer, or small molecule effector.

In certain embodiments, the binding site comprises a serpin domain which is not a reactive center loop. In other embodiments, the binding site comprises a portion of the amino-terminus of α2-antiplasmin. In certain of those embodiments, the binding site has an amino acid sequence of LGNQEPGGQTALKSPPGVCS (SEQ ID NO:1). In other embodiments, the binding site is adjacent to the site at which α2-antiplasmin cross-links to fibrin. The methods of increasing fibrinolysis are useful, for example, in a patient that has a disease or condition selected from the group consisting of myocardial infarction, thrombosis, ischemic stroke, and pulmonary embolism.

As used herein, the term "plasmin activity" refers to the serine protease activity of plasmin (e.g., in the cleavage of fibrin, fibronectin, thrombospondin, laminin, or von Willebrand factor). As used herein, the term "fibrinolysis" is used to refer to the process wherein a fibrin clot, the product of coagulation, is broken down.

As used herein, an α2-AP binding agent or molecule can include, among other molecules, antibodies (polyclonal or monoclonal). The term "antibody" (Ab) or "monoclonal antibody" (MAb) is meant to include intact molecules as well as antibody fragments (such as, for example, $F_v$, $F_{ab}$ and $F_{(ab')2}$ fragments), single chain antigen-binding proteins, "humanized" antibodies, and chimeric antibodies which are capable of specifically binding to α2-AP. $F_{ab}$ and $F_{(ab')2}$ fragments lack the $F_c$ fragment of intact antibody, clear more rapidly from the circulation, and may have less non-specific tissue binding of an intact antibody.

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies (or other binding agent) bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, "Antibodies, A Laboratory Manual" Cold Spring Harbor Publications, New York, (1988), for a description of immunoassay formats and conditions that could be used to determine selective binding.

The antibodies of the present invention may be prepared by any of a variety of methods. For example, cells expressing α2-AP (or fractions, lysates, etc. thereof) can be administered to an animal in order to induce the production of sera containing polyclonal antibodies that are capable of binding α2-AP. In a preferred method, a preparation of α2-AP of the present invention is prepared and purified to render it substantially free of natural contaminants. Such a preparation is then introduced into an animal in order to produce polyclonal antisera of greater specific activity.

The antibodies of the present invention may also be prepared using phage display technology. Methods of preparing antibodies using phage display are known in the art. See, for example, U.S. Pat. No. 5,565,332; Clarkson et al., 1991, *Nature* 352:624-628; Huse, 1989, *Science* 246:1275-1281; Kang, 1993, *Proc. Natl. Acad. Sci. USA* 88:11120-11123; Marks, 1991, *J. Mol. Biol.* 222:581-597; and McCafferty et al., 1990, *Nature* 348:552-554.

In some instances, it is desirable to prepare monoclonal antibodies (α2-AP binding molecules) from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane "Antibodies, A Laboratory Manual" Cold Spring Harbor Publications, New York, 1988. For example, monoclonal antibodies can be prepared using hybridoma technology. In general, such procedures involve immunizing an animal (preferably a mouse) with the antigen or with a cell which expresses the antigen. A preferred antigen is purified α2-AP or a fragment thereof. Suitable cells can be recognized by their capacity to secrete anti-α2-AP antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 ug/l of nonessential amino acids, about 1,000 U/ml of penicillin, and about 100 ug/ml of streptomycin. The splenocytes of such mice are extracted and fused with a suitable myeloma cell line. The method of somatic cell fusion is described in Galfre, G. and Milstein, C., Meth. Enzymol. 73:3-46 (1981). After fusion, the resulting hybridoma cells are selectively maintained in HAT medium, and then cloned by limiting dilution as described by Wands et al., 1981, Gastroenterology 80:225-232. The hybridoma cells obtained through such a selection are then assayed to identify clones which secrete antibodies capable of binding α2-AP.

Alternatively, additional antibodies capable of binding to the α2-AP antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, α2-AP-specific antibodies are used to immunize an animal, preferably a mouse. The splenocytes of such an animal are then used to produce hybridoma cells, and the hybridoma cells are screened to identify clones which produce an antibody whose ability to bind to the α2-AP-specific antibody can be blocked by the α2-AP antigen. Such antibodies comprise anti-idiotypic antibodies to the α2-AP-specific antibody and can be used to immunize an animal to induce formation of further α2-AP-specific antibodies.

It will be appreciated that Fab and $F_{(ab')2}$ and other fragments of the antibodies of the present invention may be used according to the methods disclosed herein. Such fragments are typically produced by proteolytic cleavage, using enzymes such as papain (to produce $F_{ab}$ fragments) or pepsin (to produce $F_{(ab')2}$ fragments). Alternatively, α2-AP binding fragments can be produced through the application of recombinant DNA technology, through synthetic chemistry, or biotinylation.

Also intended within the scope of the present invention are humanized or chimeric antibodies, produced using genetic constructs derived from hybridoma cells producing the MAbs described above. Humanized antibodies are antibodies in which the framework or other regions of the murine Ab is replaced with the homologous regions of a nonmurine antibody. Chimeric antibodies are antibodies in which the murine constant region has been replaced with a non-murine constant region. Methods for production of chimeric antibodies are known in the art. See, for review: Morrison, Science, 229:1202-1207 (1985); Oi et al., Bio-Techniques 4:214 (1986); see also, Cabilly et al., U.S. Pat. No. 4,816,567 (Mar. 28, 1989); Taniguchi et al., EP171496 (Feb. 19, 1986); Morrison et al., EP173494 (Mar. 5, 1986); Neuberger et al., WO8601533 (Mar. 13, 1986); Robinson et al., WO 8702671 (May 7, 1987); Boulianne et al., Nature 312:643-646 (1984); and Neuberger et al., Nature 314:268-270 (1985). Methods for production of humanized antibodies are known in the art. See, for example, U.S. Pat. No. 5,585,089; Jones et al., Nature 321:522-525 (1986); and Kettleborough et al., Protein Engineering 4:773-783 (1991).

Also provided in the present invention are single-chain antibodies capable of binding to both (1) human and non-human circulating α2-AP and (2) human and nonhuman fibrin crosslinked α2-AP. Methods of making single chain antibodies are well known in the art. See, for example, U.S. Pat. No. 4,946,778; U.S. Pat. No. 5,260,203; U.S. Pat. No. 5,091,513; and U.S. Pat. No. 5,455,030, all of which are herein incorporated by reference. Also intended within the scope of the present invention are variants of the antibodies described above.

Also provided in the present invention are α2-AP binding agent or molecules which are specifically not antibodies or fragments thereof. Screening for such α2-AP binding agents or molecules is routine in the art given the mechanism for binding and conversion of plasmin inhibitor to plasmin substrate described herein. Particular known compounds of interest or libraries of compounds generated through combinatorial chemistry techniques, for example, can be screened for the desired binding and conversion activity. Furthermore, phage display technology can be used to identify peptides, for example, for the desired binding and conversion activity. In general, phage display describes a selection technique in which a library of variants of a peptide or protein is expressed on the outside of a phage virion, while the genetic material encoding each variant resides on the inside (Sidhu et al., 2003, Chembiochem. 4:14; Ferrer et al., 1999, J. Pept. Res.: 54, 32; BouHamdan et al., 1998, J. Biol. Chem. 273: 8009). This creates a physical linkage between each variant protein sequence and the DNA encoding it, which allows rapid partitioning based on binding affinity to a given target molecule by an in vitro selection process called panning (Whaley et al., 2000, Nature, 405, 665). In its simplest form, panning is carried out by incubating a library of phage-displayed peptides with a plate (or bead) coated with the target, washing away the unbound phage, and eluting the specifically bound phage. The eluted phage is then amplified and taken through additional binding/amplification cycles to enrich the pool in favor of binding sequences. After 3-4 rounds, individual clones are characterized by DNA sequencing and ELISA. Many variations of the phage display technology are known to those of skill in the art which can be adapted for purposes of the present invention.

In one embodiment, a phage display peptide library is used such as provided by New England Biolabs (Mass, Mass.). The pre-made random peptide libraries, Ph.D. libraries, have been used for myriad similar applications, including epitope mapping, identification of protein-protein contacts (Rozinov and Nolan, 1998, Chem. Biol. 5:713-28) and enzyme inhibitors (Rodi et al., 1999, J. Mol. Biol. 285:197-203).

As used herein, the term "patient" is intended to be human or nonhuman. Preferably, the patient is human. As used herein the term "administering" refers to various means of introducing a composition into a cell or into a patient. These means are well known in the art and may include, for example, injection; tablets, pills, capsules, or other solids for oral administration; nasal solutions or sprays; aerosols; inhalants; topical formulations; liposomal forms; and the like. As used herein, the terms "effective amount" and "therapeutic amount" refer to an amount that will result in the desired result and may readily be determined by one of ordinary skill in the art.

The compositions of the present invention (e.g., plasmin activity-promoting) may be formulated for various means of administration. As used herein, the term "route" of administration is intended to include, but is not limited to subcutaneous injection, intravenous injection, intraocular injection, intradermal injection, intramuscular injection, intraperitoneal injection, intratracheal administration, epidural administration, inhalation, intranasal administration, oral administration, sublingual administration, buccal administration, rectal administration, vaginal administration, and topical administration. The preparation of an aqueous composition that contains a peptide, antibody or antibody fragment, antisense nucleic acid, receptor decoy, ribozyme, sense polynucleotide, double stranded RNA, RNAi, aptamer, or small molecule agonist, as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The compositions of the present invention (e.g., plasmin activity-promoting) can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars, or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate, and gelatin.

Prior to or upon formulation, the compositions of the present invention (e.g., plasmin activity-promoting) should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filter sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the active ingredient admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that for human administration, preparations should meet sterility, pyrogenicity, and general safety and purity standards as required by FDA Office of Biological Standards.

In some embodiments, the methods further comprise administering to the patient an agent that facilitates the degradation of fibrin, that prevents fibrin formation, or that interferes with platelet formation. In certain embodiments, the agent is selected from the group consisting of plasmin, staphylokinase, streptokinase, prourokinase, urokinase, tissue-type plasminogen activator, vampire bat plasminogen activator, heparin, hirudin, activated protein C, ticlopidine, aspirin, clopidigrel, and an inhibitor of glycoprotein IIb/IIIa function. Such thrombolytic agent may be administered separately or co-administered with the disclosed agent that increases plasmin activity.

Additional methods are provided for screening for a compound or molecule which increases fibrinolysis, comprising determining whether a compound or molecule binds to a binding site on α2-antiplasmin which increases the conversion of α2-antiplasmin from an inhibitor to a plasmin substrate, wherein the compound or molecule is not an antibody, thereby identifying a compound which increases fibrinolysis. In certain embodiments, the binding site comprises a serpin domain which is not a reactive center loop. In other embodiments, the binding site comprises a portion of the amino-terminus of α2-antiplasmin. In certain of those embodiments, the binding site has an amino acid sequence of LGNQEPGGQTALKSPPGVCS (SEQ ID NO:1). In other embodiments, the binding site is adjacent to the site at which α2-antiplasmin cross-links to fibrin. The binding of the compound to the binding site on α2-antiplasmin is determined, in some instances, by a standard binding assay.

Pharmaceutical compositions are provided that comprise an effective amount of a compound or molecule used in the disclosed methods for increasing fibrinolysis or identified by the disclosed methods for identifying a compound or molecule that increases fibrolysis. These pharmaceutical compositions are useful for treating a patient that has a disease or condition selected from the group consisting of myocardial infarction, thrombosis, ischemic stroke, and pulmonary embolism.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

General Materials and Methods

Materials

Proteins and reagents were obtained from the following suppliers: human Lys-plasmin, S-2251 (H-D-valyl-L-leucyl-L-lysine-p-nitroanilide dihydrochloride), S-2288 (H-D-I-isoleucine-P-proline-R-arginine-p-nitroanilide dihydrochloride), Chromogenix; native human $\alpha_2$-AP, Calbiochem; biotinylated peptides: $\alpha_2$-AP$_{1-12}$, $\alpha_2$-AP$_{1-32}$ (HPLC purified>95%), Advanced Chemtech; urokinase, American Diagnostica.; t-PA, BioResponse; bovine thrombin, pork trypsin, MUGB, 4-methylumbelliferyl p-guanidinobenzoate, Sigma; fresh-frozen human plasma pooled from random donors, Massachusetts General Hospital Blood Bank; [$^{125}$I] NaI, NEN-Dupont; Fold-It Screen system, Hampton Research.

Recombinant Proteins

Figure 4:
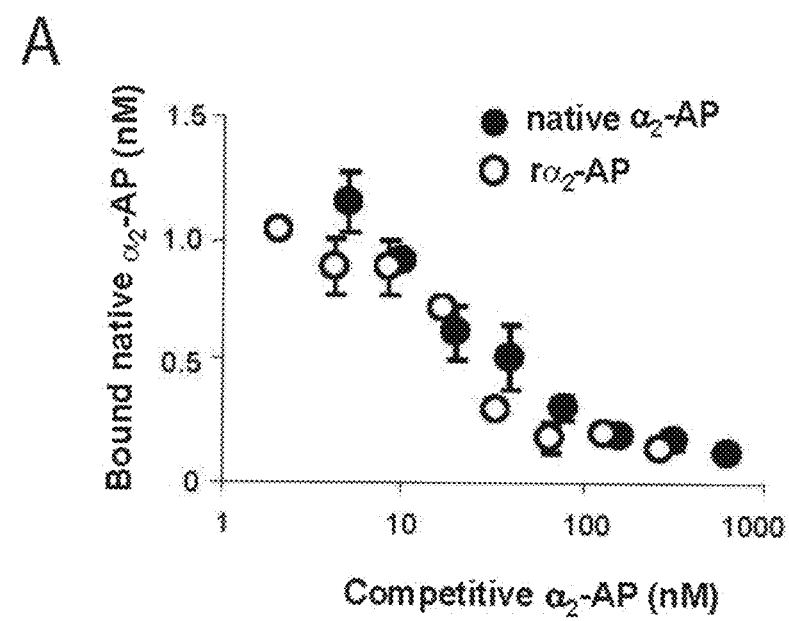
FIG. 4 analyze the binding of MAbs to $\alpha_2$-AP. Panels A and B are graphs comparing the structural determinants of the binding of MAbs to $\alpha_2$-AP constructs. MAbs 49 (Panel A) and 77 (Panel B) bind similarly to native and r$\alpha_2$-AP. MAbs were coated on the microtiter plates then nonspecific binding was blocked. Mixtures of $^{125}$I-$\alpha_2$-AP (120 nM) with varying amounts of unlabeled native (closed symbol) or recombinant (open symbol) $\alpha_2$-AP (0-160 nM; 25 µl) were added to the microtiter plate wells. After 1 hour, the bound $^{125}$I-$\alpha_2$-AP was γ-counted. The means (±S.D.) are shown. Panel C is a schematic showing the structures of human-mouse chimeras of $\alpha_2$-AP. Mouse $\alpha_2$-AP is indicated in black, human $\alpha_2$-AP is indicated in white. The demarcations of the N-terminal (NT), serpin domain (Ser), C-terminals (CT) and reactive center loop (RCL$_{352-367}$) are shown. Panel D is a bar graph showing the inhibitory activity of recombinant $\alpha_2$-APs. Plasmin (0 or 2 nM) was added to cuvettes containing recombinant $\alpha_2$-APs (0.1 mg total protein/ml) or no $\alpha_2$-AP. After 10 minutes at 37° C., S2251 (500 µM) was added, and residual plasmin activity was determined. Panel E is a bar graph showing the comparative binding of MAb RWR to immobilized r$\alpha_2$-APs and amino-terminal peptides. Recombinant wild type $\alpha_2$-APs or chimeras were absorbed on the microtiter plates, the nonspecific binding was blocked, and MAb (RWR or Dig-control) were added for 1 hour. The bound MAb was γ-counted as described below. The means (±S.D.) are shown. Panel F are immunoblots, showing the binding of MAbs 77 and 49 to various recombinant $\alpha_2$-APs. Purified active recombinant $\alpha_2$-AP molecules (10 μg) were subjected to SDS-PAGE (12% gel) under non-reducing conditions and electroblotted. The blots were treated with 77 or 49 MAbs and exposed using goat anti-mouse antibody. Panel G is a table, showing a summary of the binding of MAbs to $\alpha_2$-AP chimeras. A "+" indicates that MAb strongly bound to the $\alpha_2$-AP construct, whereas a "−" indicates that there was no binding. No binding was seen with an anti-digoxin MAb (Dig) that was used as a negative control.
Figure 4:
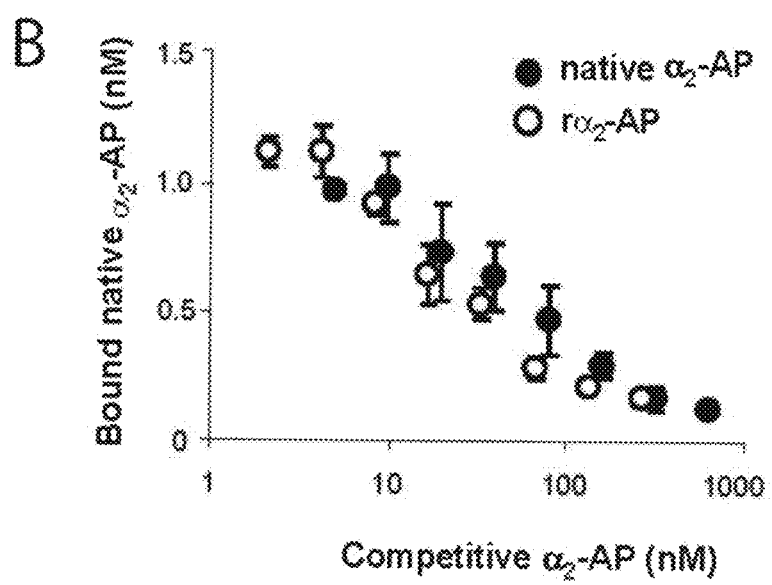

The $\alpha_2$-AP sequence was modeled on the serpin structural coordinates (Huntington et al., 2000, Nature 407:923-926) using a ClustalW program (www.ch.embnet.org). Mouse $\alpha_2$-AP sequence was cloned from mouse IMAGE cDNA clones (Open Biosystems) using GTCATATGGCCCAGCA-GAAGCTG (SEQ ID NO:2) and CTCGAGCTGGCA-GGGGAGGAC (SEQ ID NO:3) primers. Human $\alpha_2$-AP was chimerized with the corresponding sequences of mouse $\alpha_2$-AP by PCR with overlap extension. The structural domains of $\alpha_2$-APs are shown in FIG. 4A. The associated sense and antisense PCR primers were, respectively:

```
                                        (SEQ ID NO: 4)
NT_h-GTCATATGAACCAGGAGCAGGTG
and
                                        (SEQ ID NO: 5)
GTCTCCTCTGCAGTTGGGTCTCTGCTGCAGACTCC;

(SEQ ID NO: 6)
NT_m-GTCATATGGCCCAGCAGAAGCTG
and
                                        (SEQ ID NO: 7)
TCTGCTCTGGAGTTGGGACACTCTT;

(SEQ ID NO: 8)
Ser_h-AACTCCAGAGCAGACCCAC
and
                                        (SEQ ID NO: 9)
TTATAAAGAAGAGGAAGGGGCG;

(SEQ ID NO: 10)
Ser_m-CCAACTGCAGAGGAGAC
and
                                        (SEQ ID NO: 11)
CCTGTGGTGTCCTCGAAGATGAAGAAGAGGAAGGG;

(SEQ ID NO: 12)
CT_h-TTCGAGGACACCACAGGC
and
                                        (SEQ ID NO: 13)
ATCCTCGAGGAGCCGTGG;

(SEQ ID NO: 14)
CT_m-CGCCCCTTCCTCTTCTTTATAA
and
                                        (SEQ ID NO: 15)
CTCGAGCTGGCAGGGGAGGAC.
```

PCR products were sequenced and ligated into the pET-16b vector (kind gift of Dr. G. Matsueda, Princeton, N.J.) for bacterial expression in BL21 cells. The r$\alpha_2$-APs were purified as His-fusion proteins from the insoluble pellets of the bacterial lysate and refolded using Fold-It Screen system. Finally all r$\alpha_2$-APs were dialyzed in TBS buffer (50 mM Tris, 100 mM NaCl, pH 7.4), analyzed by SDS-PAGE. The activity of the refolded protein was determined by assays with Lys-plasmin. Recombinant micro-plasminogen was produced as described (Reed et al., 1999, Proc. Natl. Acad. Sci. (USA) 96:8879-8883), activated to micro-plasmin by catalytic amounts of urokinase coupled to protein-A sepharose, and titrated by a fluorogenic substrate as described Turner et al., 2002 J Biol Chem. 277:33068-33074.

Antibodies

MAbs were generated by somatic cell fusion, selected for specific binding to $\alpha_2$-AP, cloned and purified as described (Reed, G. L. Functional characterization of monoclonal antibody inhibitors of alpha 2-antiplasmin that accelerate fibrinolysis in different animal plasmas. *Hybridoma* 1997; 16: 281-286). The serotypes of these MAbs were: 49 ($Ig_{\gamma 2a}K$), 77($Ig_{\gamma 2a}K$), RWR ($Ig_{\gamma 1a}K$). Polyclonal antibodies were generated against peptides that mimic the NH2-terminus (NQEQVSPLTLLKLG) (SEQ ID NO:16) and COOH-terminus (GDKLFGPDLKLVPPMEEDYPQFGSPK) (SEQ ID NO:17) as described (Reed et al. 1992, *Thromb Haemost* 68:315-320).

Protein Radiolabeling

Native human $\alpha_2$-AP was radioiodinated to a specific activity of $1.8 \times 10^6$ cpm/µg (Lukacova et al., 1991, *Biochemistry* 30:10164-10170).

Binding Assays

Binding of Native $\alpha_2$-AP to MAbs:

MAbs (RWR, 49, 77 and Dig-control) (3 µg/ml; 50 µl) were absorbed on microtiter plates for 1 h. Nonspecific binding was blocked. Then $^{125}I$-$\alpha_2$-AP (0.08-500 nM; 50 µl) was added. After 1 h. the bound $^{125}I$-$\alpha_2$-AP was γ-counted.

Direct Binding of MAbs to Various $\alpha_2$-AP Structures:

Various r$\alpha_2$-APs, or $\alpha_2$-AP peptides ($\alpha_2$-$AP_{1-12}$ and $\alpha_2$-$AP_{1-32}$) (5 µg/ml; 50 µl) or no protein (control) were absorbed on microtiter plates for 1 h. After blocking and washing, MAbs (RWR, 49, 77 and Dig-control) (3 µg/ml; 50 µl) were added for 1 h. After additional washing, bound MAb was detected by $^{125}I$-F(ab)' goat anti-mouse Ig (100, 000 cpm/50 µl) followed by γ-counting.

Comparative Binding of MAbs to Native and Recombinant $\alpha_2$-AP.

MAbs 49 or 77 (3 µg/ml; 50 ul) were absorbed on plates for 1 h. Nonspecific binding was blocked. Mixture of $^{125}I$-$\alpha_2$-AP (12 nM; 25 µl) with varying amounts of unlabeled native or recombinant $\alpha_2$-AP (0-1000 nM; 25 µl) were added to the microtiter plate for 1 h. Then plates were washed and bound $^{125}I$-$\alpha_2$-AP was γ-counted.

The Binding of MAbs to Native $\alpha_2$-AP and $\alpha_2$-AP-Plasmin Complex:

MAbs (RWR, 77, 49 or Dig-control) (3 µg/ml; 50 µl) were absorbed on plates for 1 h. Nonspecific binding was blocked. Human plasmin (0 and 350 nM) was pre-incubated with $^{125}I$-$\alpha_2$-AP (75 nM) for 30 min at 25° C. Then 50 µl of this mixture was added to the microtiter plates with coated MAbs for 1 h. After additional washing bound $^{125}I$-$\alpha_2$-AP was γ-counted.

Inhibition Studies

Native $\alpha_2$-AP (1.8 µM) was pre-incubated with or without of MAbs (49, 77, Dig-control; 1.8 µM or RWR 1.8 µM and 18 µM) for 60 min at 4° C. The fast inhibition of plasmin, micro-plasmin and trypsin was examined by a continuous method as described (Wiman, B. and Collen, D. On the kinetics of the reaction between human antiplasmin and plasmin. *Eur J Biochem* 1978; 84: 573-578). The serine protease (20 nM) was added to a cuvette containing S-2251 (500 µM) in 300 µl of TBS buffer, and the change in absorbance at 405 nm was recorded at 0.1-min intervals prior to and after the addition of 10 µl of $\alpha_2$-AP (1.8 µM) or preformed $\alpha_2$-AP/MAb complex. The final concentration of $\alpha_2$-AP in the cuvette was 60 nM. The percentage of residual protease activity was calculated from the initial value (defined as 100%). The inhibition constant (i.e., $k_1$, the rate constant of reversible complex formation) was determined as described (Turner et al., 2002, *J Biol. Chem.* 277:33068-33074).

To investigate how the MAbs affected the ability of $\alpha_2$-AP to inhibit plasmin-catalyzed hydrolysis, plasmin (3 nM) was added to cuvettes containing S-2251 (500l.1M) with equimolar mixtures of $\alpha_2$-AP and MAb49 (84 nM) in TBS buffer as described (Rijken et al., 1988, *Biochem J* 255:609-615). The change in absorbance at 405 nm was recorded.

Measurement of Stoichiometry of Inhibition

The stoichiometry of inhibition ($SI=1+k_s/k_i$) represents the partition ratio of the serpin for the suicide inhibitory vs. the substrate pathway (Schechter and Plotnick, 2004, *Methods* 32:159-168). To determine the effect of MAbs on the inhibitory mechanism of $\alpha_2$-AP, SI values were calculated as a ratio of the number of moles of $\alpha_2$-AP required for inactivation of one mole of plasmin in the presence and absence of the MAbs. Equimolar complexes (0-750 nM) of native $\alpha_2$-AP with RWR, 49 or 77 MAbs were prepared and titrated with the same amount of plasmin (10 nM) using S-2251 substrate (500 µM). SI values were defined as the x-intercept of the graph of residual plasmin activity versus [$\alpha_2$-AP]/[plasmin] ratio as described (Schechter and Plotnick, 2004, *Methods* 32:159-168).

Western Blot Analysis of $\alpha_2$-AP Cleavage

Native human $\alpha_2$-AP (230 nM) was incubated with micro-plasmin (30 nM) in the absence of MAbs for 60 min at 25° C. In parallel studies, micro-plasmin (30 nM) was added to a premixed human $\alpha_2$-AP (230 nM) with corresponding amounts of MAbs (RWR, 2.5 µM; 49MAb, 500 nM; 77MAb, 500 nM or Dig-control, 2.5 µM) and incubated for 60 min at 25° C. The samples were applied on a SDS-PAGE under reducing conditions and electroblotted. The blots were blocked, treated with rabbit polyclonal antibody to the amino-terminal or to the carboxy-terminal residues of $\alpha_2$-AP, and examined using a phosphorimager system (Amersham, UK).

Clot Lysis

Human plasma (250 µl) was pre-incubated with MAbs (0 or 80 µg) for 15 min at 37° C. Then Lys-plasmin (200 nM) or t-PA (0.1-8 nM) was added together with thrombin (2 U/ml) and $CaCl_2$ (1 mM) to a final volume of 500 µl. The clot turbidity ($A_{405 \, nm}$) was monitored at 37° C. The maximum and minimum absorbance values for turbidity were defined as equal to 0 and 100% clot lysis respectively.

Example 1

Effect of MAbs on the Inhibition of Plasmin by $\alpha_2$-AP $\alpha_2$-AP (60 nM) rapidly inhibited plasmin (20 nM) activity within seconds (FIG. 1A, curve 1). A control MAb (anti-digoxin, Dig) (Reed et al., 1997, *Hybridoma* 16:281-286) had no significant effect on these interactions (FIG. 1A, curve 2). Stoichiometric amounts of RWR MAb slightly increased the half-life of the reaction ($t_{1/2}$, time to 50% loss of plasmin activity) to 1 minute (FIG. 1A; curve 3 and inset). Higher concentrations (600 nM) of RWR more effectively neutralized the effects of $\alpha_2$-AP (FIG. 1A; curve 4) and prolonged $t_{1/2}$ to 9 minutes (FIG. 1A, inset). In contrast 49 and 77 MAbs (FIG. 1A, curves 5,6) were more potent and almost completely prevented the inhibition of plasmin by $\alpha_2$-AP at equimolar concentrations; this preserved the activity of plasmin for greater than 9 minutes (the duration of these experiments, FIG. 1A, inset). However, when MAbs were added to the preformed plasmin-$\alpha_2$-AP complex, no regeneration of plasmin activity was detected (data not shown).

Example 2

Effect of MAbs on the Ability of $\alpha_2$-AP to Inactivate Other Serine Proteases The fast inhibition of plasmin by $\alpha_2$-AP involves interactions between the kringle domains of plasmin and Lys$_{346}$ and Lys$_{452}$ in the unique C-terminal extension of $\alpha_2$-AP (Wiman and Collen, 1978, *Eur. J. Biochem.* 84:573-578; Frank et al., 2003, *Biochemistry* 42:1078-1085). However, $\alpha_2$-AP also inhibits proteases that do not contain kringles (e.g., micro-plasmin and trypsin, an archetypal serine protease). In the absence of MAb, or in the presence of the control (Dig) MAb, $\alpha_2$-AP (60 nM) completely quenched the activity of all three enzymes tested (20 nM; FIG. 1B): plasmin ($k_1$>2600±550 mM$^{-1}$s$^{-1}$), micro-plasmin ($k_1$=33±1 mM$^{-1}$s$^{-1}$), and trypsin ($k_1$=476±77 mM$^{-1}$s$^{-1}$). RWR (600 nM), 49 and 77 (60 nM) prevented $\alpha_2$-AP from inactivating these proteases (by 40-95%).

Example 3

MAbs Accelerate Plasma Clot Lysis Induced by Plasmin and t-PA

Figure 2:
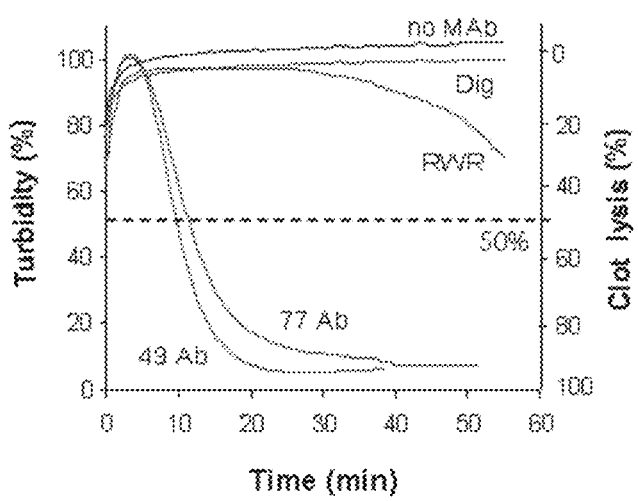
FIG. 2 shows the effect of MAbs on plasma clot lysis by plasmin. Panel A is a graph showing the effect of MAb 49, MAb 77, and MAb-RWR Different MAbs (600 nM) were incubated with human plasma before clotting. Then Lys-plasmin (200 nM) was added and plasma was immediately clotted by thrombin. The lysis of clot was detected at 37° C. by a decrease in turbidity. Panel B is a graph showing the influence of 49 MAb on the time of 50% clot lysis induced by t-PA. Human plasma was incubated with Dig-control or 49 MAb (600 nM) before clotting. Then thrombin and t-PA (0.1-8 nM) were added and clot turbidity was monitored as described above. The time required for 50% clot lysis was plotted versus the t-PA dose.
Figure 2:
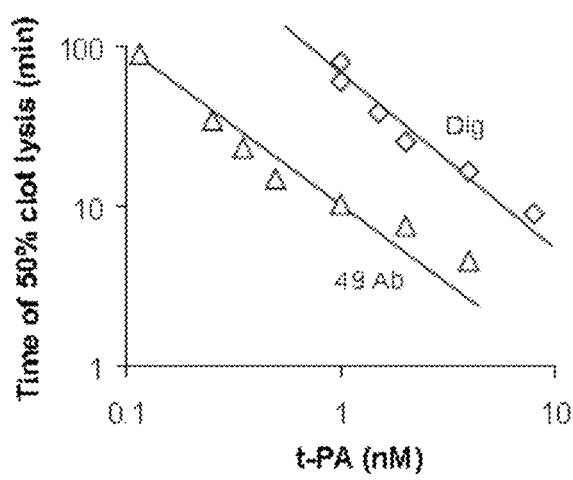

Fibrin is the physiological substrate of plasmin, therefore inactivation of $\alpha_2$-AP should preserve the activity of plasmin and enhance fibrinolysis in human plasma clots. Plasmin alone, or in the presence of the control Dig-MAb, did not initiate significant clot lysis (FIG. 2A). RWR, in 10-fold molar excess of $\alpha_2$-AP, enhanced fibrinolysis (as reflected by a decrease in clot turbidity). In contrast, MAbs 49 and 77 markedly accelerated fibrinolysis when present in stoichiometric amounts with $\alpha_2$-AP, causing 50% plasma clot lysis by 10 and 12 min respectively. MAb 49 also significantly accelerated clot lysis initiated t-PA (FIG. 2B) and reduced the time required for 50% clot lysis by 7.5-fold on average. In these experiments the pro-fibrinolytic effects of these MAbs in human plasma paralleled their potency for inhibiting $\alpha_2$-AP in vitro.

Example 4

The Structural Requirements for the Binding of MAbs to $\alpha_2$-AP

Figure 3:
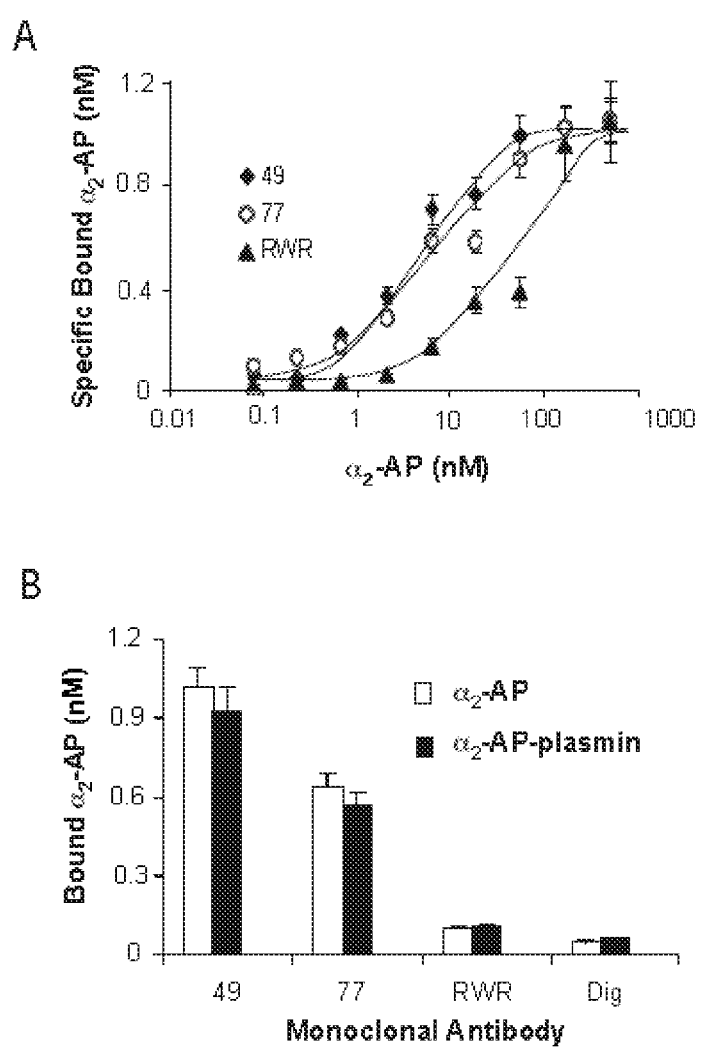
FIG. 3 shows the binding of MAbs to native $\alpha_2$-AP in solution or to $\alpha_2$-AP and the $\alpha_2$-AP/plasmin complex. Panel A is a graph showing the binding of MAbs to native $\alpha_2$-AP in solution. MAbs were absorbed on microtiter plates. Nonspecific binding was blocked and $^{125}$I-$\alpha_2$-AP (0.08-500 nM) was added. After washing, the amount of bound $\alpha_2$-AP was determined by γ-counting. The specific binding of 49, 77 and RWR was calculated by deduction of nonspecific binding of $^{125}$I-$\alpha_2$-AP to Dig (control) MAb. Panel B is a graph showing the binding of MAbs to $\alpha_2$-AP and the $\alpha_2$-AP/plasmin complex. MAbs were absorbed on microtiter plates. A complex of $^{125}$I-$\alpha_2$-AP and human plasmin was formed and pre-incubated for 30 min at 25° C. Then $^{125}$I-$\alpha_2$-AP alone or equivalent amounts of formed $^{125}$I-$\alpha_2$-AP-plasmin complex were added. After washing the bound $^{125}$I-$\alpha_2$-AP was γ-counted.

To further understand the difference in the action of these MAbs we examined their binding to $\alpha_2$-AP. RWR, 49 and 77 bound to active $^{125}$I-$\alpha_2$-AP in solution in a dose-dependent manner. The apparent affinity of 49 ($K_d$=1.7±0.3 nM) and 77 ($K_d$=2.5±0.5 nM) for $^{125}$I-$\alpha_2$-AP was 5-8 fold higher than was the affinity of RWR ($K_d$=13±4 nM) (FIG. 3A), which was consistent with the differences in the observed potency of these MAbs for inhibiting $\alpha_2$-AP. Despite differences in the affinity, each of these 3 MAbs bound with similar apparent avidity to free $\alpha_2$-AP and to the preformed $\alpha_2$-AP-plasmin complex (FIG. 3B). This indicates that the binding of the MAbs to $\alpha_2$-AP was not simply competitive with plasmin.

Recombinant $\alpha_2$-AP chimeras were created to examine the structural elements in $\alpha_2$-AP recognized by these MAbs. First we established that MAbs 49 and 77 bound to native human $\alpha_2$-AP and to recombinant human $\alpha_2$-AP (h$\alpha_2$-AP$_{1-452}$) with comparable binding avidity (FIG. 4A, 4B). Then we took advantage of the fact that these MAbs bound selectively to human $\alpha_2$-AP but not mouse $\alpha_2$-AP (FIGS. 4E, F). Different mouse/human $\alpha_2$-AP chimeric molecules were created, purified, refolded and probed for their ability to inhibit human plasmin (FIGS. 4C,D). In solid-phase binding assays RWR bound specifically to human r$\alpha_2$-AP$_{1-452}$ and to r$\alpha_2$-AP$_{\Delta 402-452}$ (a structure that is lacking part of the CT-domain that contains the plasmin kringle-binding sites), as well as two chimeric constructs (NT$_h$-Ser$_m$-CT$_m$, NT$_h$-Ser$_m$-CT$_h$). These data localized the RWR binding epitope within in the NT-domain of human $\alpha_2$-AP (FIGS. 4E, G). Direct binding assays showed that RWR bound to a peptide mimicking $\alpha_2$-AP residues 1-32 (NQEQVSPLTLLKLGNQEPGGQTAKLSPPGVCS) (SEQ ID NO:18) of Asn-$\alpha_2$-AP (Koyama et al., 1994, *Biochem Biophys Res Commun* 200:417-422) but not to a peptide spanning residues 1-12 (NQEQVSPLTLLK) (SEQ ID NO:19). This indicated that RWR recognized a continuous epitope in human $\alpha_2$-AP between residues 13-32 (LGNQEPGGQTAKLSPPGVCS) (SEQ ID NO:1). It is interesting to note that the sequences of mouse and human $\alpha_2$-AP differ at slightly more than half of the residues in this short peptide.

Immunoblotting experiments established that MAbs 49 and 77 bound to $\alpha_2$-AP structures containing the human serpin domain such as human r$\alpha_2$-AP$_{1-452}$, r$\alpha_2$-AP$_{\Delta 405-452}$, or the NT$_m$-Ser$_h$-CT$_m$ or NT$_m$-Ser$_h$ chimeras (FIG. 4F). They did not bind to chimeras containing only the human NT-domain or the human CT-domain. Taken together MAb 49 and 77 recognized nonlinear or conformation-dependent epitopes in the human serpin domain. The serpin domain contains the RCL (P14-P3') of $\alpha_2$-AP which is the target for plasmin interactions and a possible binding site of these MAbs. The C-terminal part of RCL (P1-P3') of human, mouse and bovine $\alpha_2$-APs are identical. However, this region is unlikely to be the binding epitope because MAbs 49 and 77 did not bind to either mouse (FIG. 4F) or bovine $\alpha_2$-AP (not shown). FIG. 4G summarizes the binding of MAbs to various $\alpha_2$-AP chimeras.

Example 5

Influence of MAbs on the Interaction of $\alpha_2$-AP with Plasmin

Figure 5:
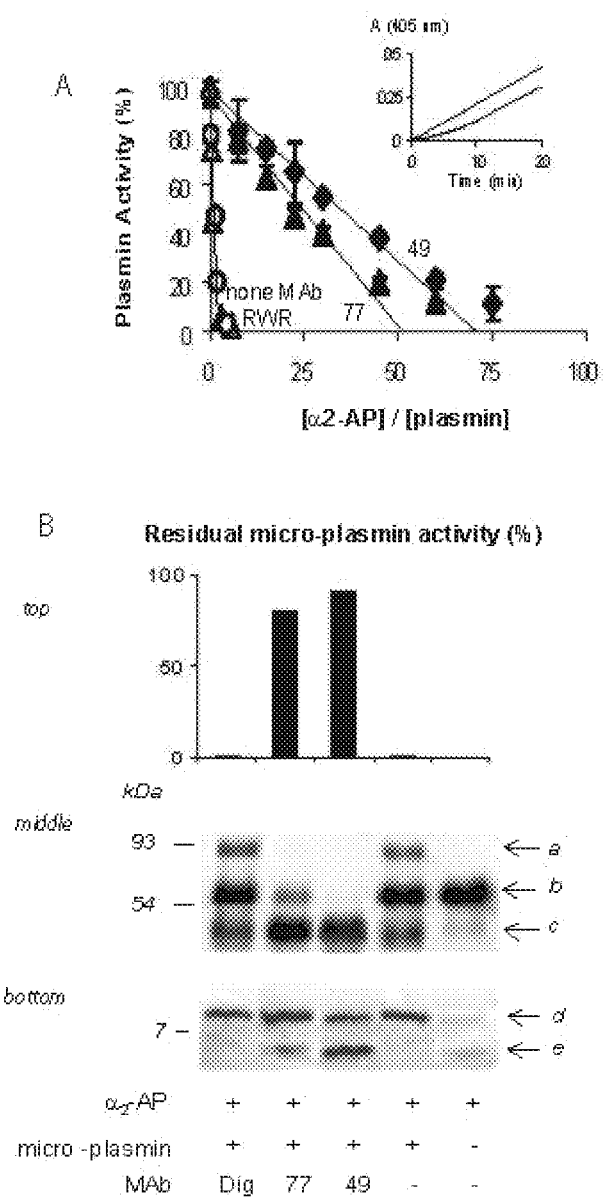
FIG. 5 demonstrates the influence of MAbs on the interaction of human plasmin with $\alpha_2$-AP. Panel A is a graph showing the effects of MAbs on the stoichiometry of inhibition (SI) of plasmin by $\alpha_2$-AP. Equimolar complexes (0-750 nM) of native $\alpha_2$-AP with MAbs were prepared and titrated with the same amount of plasmin (10 nM) using S-2251 substrate (500 μM). The percentage of residual plasmin activity was plotted as a function of the [$\alpha_2$-AP]/[plasmin] ratio for each reaction. Inset: Recorder trace of change in plasmin activity (3 nM) without (upper curve) or with (lower curve) or an equimolar mixture of $\alpha_2$-AP with MAb 49 (84 nM). Panel B shows a bar graph and immunoblot analysis of the effects of MAbs on the interaction of $\alpha_2$-AP with micro-plasmin. Native human $\alpha_2$-AP (230 nM) was incubated with micro-plasmin (30 nM) in the absence or presence of MAbs 49, 77 or control as described under "Material and Methods." Samples of these reactions were examined for residual plasmin amidolytic activity (top panel) or electrophoresed on SDS-PAGE (12% or 15%) gels under reducing conditions. After electroblotting, membranes were developed using polyclonal antibody to the amino-terminus (middle panel) or to the carboxy-terminus (bottom panel) of $\alpha_2$-AP. The relative migration the covalent $\alpha_2$-AP/micro-plasmin complex (a), native $\alpha_2$-AP (b), cleaved $\alpha_2$-AP ~55 kDa (c) and carboxy-terminal peptides ~8 kDa (d) and ~6 kDa (e) are indicated on the right.

As noted early (FIG. 3B) the nearly equivalent, high avidity binding of MAbs 49 and 77 to $\alpha_2$-AP and the $\alpha_2$-AP-plasmin complex suggested that these MAbs did not simply compete with plasmin for $\alpha_2$-AP binding. Consequently we examined the effect of these MAbs on the mechanism of plasmin inhibition by $\alpha_2$-AP by determining the stoichiometry of inhibition (SI=1+$k_{sub}/k_{inh}$) for these MAbs (Schechter and Plotnick, 2004, *Methods* 32:159-168). The SI value for the inhibition of plasmin by $\alpha_2$-AP alone was 1.1±0.1, (FIG. 5A). RWR (10-fold molar excess to $\alpha_2$-AP) slightly increased the SI value (1.7±0.3). However, stoichiometric quantities of MAbs 77 and 49 markedly increased the SI values to 51±4 and 67±7, respectively. These SI values indicated that MAbs 49 and 77 almost completely (98-99%) shifted the serpin-protease reaction from the inhibitor to the substrate pathway. Consistent with this notion, we found only transient inhibition of plasmin amidolytic activity for S2251 by native $\alpha_2$-AP in the presence of MAb 49 (FIG. 5A, inset). In contrast the low SI values obtained for MAb RWR indicate that it did not markedly shift the serpin-protease reaction to the substrate pathway and raise the possibility that this MAb may inhibit a2AP through other mechanisms.

To confirm these findings we examined the plasmin-$\alpha_2$-AP interaction by SDS-PAGE and immunoblotting. Previous studies have shown that when excess $\alpha_2$-AP is incubated with plasmin, there are 5 forms of $\alpha_2$-AP detectable: $\alpha_2$-AP-plasmin complex, native $\alpha_2$-AP, cleaved $\alpha_2$-AP (relative mass ($M_r$) of ~55 kDa) and two smaller $\alpha_2$-AP fragments of $M_r$~8 kDa and $M_r$~6 kDa (Wiman and Collen, 1978, *Eur J Biochem* 84:573-578; Holmes et al., 1987, *Science* 238:209-

211). Consistent with these data, incubation of human micro-plasmin with excess $\alpha_2$-AP (with or without a control MAb) lead to the formation of a stable covalent $\alpha_2$-AP-micro-plasmin complex (FIG. 5b, middle panel) that was larger than $\alpha_2$-AP alone (a), uncleaved $\alpha_2$-AP (b), cleaved $\alpha_2$-AP (c) and, the cleaved COOH-terminal peptides of $\alpha_2$-AP (FIG. 5b, bottom panel) (d) and (e). Control experiments showed that, in the absence of MAbs, the inhibited covalent microplasmin-$\alpha_2$-AP complex did not dissociate during 60 min. of observation. In contrast, MAbs 49 and 77 significantly reduced the formation of the inhibited covalent $\alpha_2$-AP-micro-plasmin complex and induced limited proteolysis of native $\alpha_2$-AP with enhanced formation of the $M_r$~55 kDa, ~8 kDa and ~6 kDa $\alpha_2$-AP fragments (FIG. 5b, middle and bottom panels). When the residual amidolytic activity of micro-plasmin was measured at the end of reaction ~80-90% of micro-plasmin activity was preserved in samples containing MAbs 49 and 77, whereas there was no significant residual activity in samples containing the control MAb or no MAb (FIG. 5b, top panel). Addition of each of the MAbs to the preformed inhibited $\alpha_2$-AP/microplasmin complex did not enhance the cleavage of the complex indicating that active micro-plasmin was required for this effect (data not shown). Taken together these experiments indicate that these MAbs prevent formation of the inactive $\alpha_2$-AP-plasmin complex and convert $\alpha_2$-AP from a plasmin inhibitor to a substrate.

These experiments reveal that MAbs that bind to different structural elements in the $\alpha_2$-AP molecule convert $\alpha_2$-AP from a plasmin inhibitor to a plasmin substrate. In solutions containing $\alpha_2$-AP, these MAbs significantly preserve the activity of plasmin. This explains the ability of these MAbs to markedly amplify fibrinolysis in plasma clots induced by plasminogen activators (Reed et al., 1990, Proc Natl Acad Sci USA 87:1114-1118).

When compared with RWR, both MAbs 49 and 77 were more potent $\alpha_2$-AP inhibitors and had greater effects on fibrinolysis than RWR. MAbs 49 and 77 bound preferentially, in a conformation-selective manner, to the serpin domain of $\alpha_2$-AP. Although MAbs 49 and 77 potently inhibited the interaction of plasmin with active $\alpha_2$-AP, they could bind as well to the $\alpha_2$-AP/plasmin covalent complex, despite the fact that covalent complex formation results in the cleavage of the RCL and would be predicted to induce a substantial loss (~40%) in the structure of the serpin (Huntington et al., 2000, Nature 407:923-926). Thus the interaction of MAbs 49 and 77 with $\alpha_2$-AP did not require an intact reactive center loop, and did not affect the interaction of the plasmin active site with the $Arg_{364}$-$Met_{365}$ in P1-P1'.

RWR was significantly less potent (>10-fold) than 49 and 77 as an inhibitor of $\alpha_2$-AP and was less potent for enhancing fibrin degradation by plasmin or t-PA in human plasma clots. RWR had less apparent binding affinity for $^{125}$I-$\alpha_2$-AP in solution-phase assays but it bound much more avidly in solid-phase assays to immobilized $\alpha_2$-AP and was the only antibody that bound to fully denatured forms of $\alpha_2$-AP. Epitope mapping experiments showed that RWR bound to a continuous $NH_2$-terminal sequence (13-32) near the site at which $\alpha_2$-AP($Gln_2$) is crosslinked to fibrin. This site would be predicted from other serpin structures to be at some distance from the 'active' site of $\alpha_2$-AP (Lee et al., 2000, J Biol Chem 275:37382-37389). The fact that RWR inhibited $\alpha_2$-AP activity indicates that contact interactions of the MAb with the $NH_2$-terminus $\alpha_2$-AP, at sites distinct from the known contact sites of $\alpha_2$-AP with plasmin, are sufficient to block the action of this serpin. Unfortunately, because of a paucity of structural data, the spatial relationships between the $NH_2$-terminus and the serpin domain of $\alpha_2$-AP are unknown. It is interesting to note that the $NH_2$-terminus of $\alpha_2$-AP is a functionally distinct domain that contains the residues ($Gln_2$ and $Gln_{21}$) that activated factor XIII uses to crosslink $\alpha_2$-AP to fibrin (Lee et al., 2000, J Biol Chem 275:37382-37389).

Although there is little known about the 3-dimensional structure of $\alpha_2$-AP, studies of related molecules have shown that serpin structure and function is more complex and dynamic than had been appreciated. The high affinity interactions of an MAb with a serpin such as $\alpha_2$-AP may act to perturb serpin function through several mechanisms including 1) accelerating the conversion of the serpin from an active to latent form (Verhamme et al., 1999, J Biol Chem 274:17511-17517); 2) preventing the formation of a Michaelis inhibitory complex between the serpin and protease (Bijnens et al., 2001, J Biol Chem 276:44912-44918); 3) promoting the dissociation the intermediate acyl-protease-serpin complex leading to hydrolysis of the serpin and liberation of active protease (Komissarov et al., 2002, J Biol Chem 277:43858-43865); 4) altering the ability of the serpin to bind to other regulatory molecules (Ngo et al., 2001, J Biol Chem 276:26243-26248). Our results suggest that MAbs 49 and 77 act through the $3^{rd}$ mechanism to convert $\alpha_2$-AP to a plasmin substrate. The interactions of $\alpha_2$-AP with MAbs 49 and 77 almost completely (98-99%) shift the reaction to the substrate pathway and prevent the formation of the final covalent acyl-protease-serpin complex. A similar mechanism has been described for the serpin-protease interaction between PAI-1 and t-PA where MAbs convert PAI-1 from an inhibitor into substrate (Komissarov et al., 2002, J Biol Chem 277:43858-43865). It is interesting to note that these $\alpha_2$-AP MAbs simulate a genetic cause of $\alpha_2$-AP deficiency which converts $\alpha_2$-AP to a plasmin substrate by a point mutation (Holmes et al., 1987, Science 238:209-211). Given that experimental $\alpha_2$-AP deficiency or $\alpha_2$-AP neutralization markedly increase the concentration of active plasmin, enhances fibrinolysis and protects against experimental ischemic stroke, this type of inhibition may have therapeutic value in cardiovascular diseases (Butte et al., 1997, Circulation 95:1886-1891; Reed et al., 1988, Trans Assoc Am Physicians 101:250-256; Reed et al., 1990, Circulation 82:164-168).

In addition, in mice, α2AP-deficiency also has the desirable property of accelerating wound healing, perhaps through an increase in the release of vascular endothelial growth factor. Inhibitors of mouse α2AP accelerated the rate of liver healing after injury when compared to controls. Deficiency of α2AP also decreased arteriosclerosis (neointimal proliferation) after vascular injury.

For the purposes of this application, one of the most profound and intriguing results of α2AP deficiency or depletion is that it markedly reduced ischemic stroke size, even if there is no reperfusion. In contrast, TPA increased stroke size—which may be attributable to TPA's neurotoxic effects.

When many new therapies are developed, there is no indication of how they might work in humans prior to clinical trials. However, the data on humans with α2AP deficiency provides a compelling argument that transient α2AP deficiency would be safe and effective for dissolving clots. There is additional data in mice that complete α2AP deficiency is safe and, that α2AP-deficient mice can be safely treated with TPA without increasing bleeding risk. Moreover, α2AP deficiency reduces ischemic stroke size, reduces mortality from experimental pulmonary embolism, protects against arteriosclerosis, and accelerates wound healing.

What is claimed is:

1. A method of converting an α2-antiplasmin molecule from a serine protease inhibitor to a serine protease substrate in a human patient in need thereof, comprising:
   a) selecting a monoclonal antibody for an ability to specifically bind to a human α2-antiplasmin molecule at a binding site to convert the human α2-antiplasmin molecule from a serine protease inhibitor to a serine protease substrate,
   b) determining an effective amount of the monoclonal antibody for increasing the conversion of the α2-antiplasmin molecule from the serine protease inhibitor to the serine protease substrate in the patient, and
   c) administering to the patient the effective amount of the selected monoclonal antibody, thereby increasing serine protease activity to increase fibrin degradation products in the patient.

2. The method of claim 1, wherein the binding site comprises a serpin domain that does not include a reactive center loop of the α2-antiplasmin molecule.

3. The method of claim 1, wherein the binding site comprising the amino-terminus of α2-antiplasmin.

4. The method of claim 1, wherein the binding site is adjacent to the site at which α2-antiplasmin cross-links to fibrin.

5. The method of claim 4, wherein the binding site has an amino acid sequence of LGNQEPGGQTALKSPPGVCS (SEQ ID NO:1).

6. The method of claim 1, wherein the method modulates vessel remodeling, cell migration, wound and organ healing, growth factor function, angiogenesis, tumor growth and dissemination, or infection.

7. The method of claim 1, wherein the patient has a disease or condition selected from the group consisting of thrombosis, myocardial infarction, venous thrombosis, arterial thrombosis, ischemic stroke, and pulmonary embolism.

8. The method of claim 1, further comprising administering to the patient an agent that facilitates the degradation of fibrin, that prevents fibrin formation, or that interferes with platelet formation.

9. The method of claim 8, wherein the agent is selected from the group consisting of plasmin, staphylokinase, streptokinase, prourokinase, urokinase, tissue-type plasminogen activator, vampire bat plasminogen activator, heparin, hirudin, activated protein C, ticlopidine, aspirin, clopidigrel, thrombin activatable fibrinolysis inhibitors, and an inhibitor of glycoprotein IIb/IIIa function.

10. The method of claim 1, wherein the serine protease is plasmin.

11. The method of claim 1, wherein the monoclonal antibody comprises Fv fragments of MAb 49 or MAb 77.

12. A method of treating a human patient by modulating vessel remodeling, cell migration, wound and organ healing, growth factor function, angiogenesis, tumor growth and dissemination, or infection, comprising:
   a) selecting a monoclonal antibody for an ability to specifically bind to a human α2-antiplasmin molecule at a binding site to convert the human α2-antiplasmin molecule from a serine protease inhibitor to a serine protease substrate,
   b) determining an effective amount of the monoclonal antibody for modulating vessel remodeling, cell migration, wound and organ healing, growth factor function, angiogenesis, tumor growth and dissemination, or infection by increasing the conversion of the α2-antiplasmin molecule from the serine protease inhibitor to the serine protease substrate in the patient, and
   c) administering to the patient an effective amount of a pharmaceutical composition comprising the effective amount of the selected monoclonal antibody.

13. The method of claim 12, wherein the serine protease is plasmin.

14. The method of claim 12, wherein the binding site comprises a serpin domain that does not include a reactive center loop of the α2-antiplasmin molecule.

15. The method of claim 12, wherein the binding site comprising the amino-terminus of α2-antiplasmin.

16. The method of claim 12, wherein the binding site is adjacent to the site at which α2-antiplasmin cross-links to fibrin.

17. The method of claim 16, wherein the binding site has an amino acid sequence of LGNQEPGGQTALKSPPGVCS (SEQ ID NO:1).

18. The method of claim 12, wherein the monoclonal antibody comprises Fv fragments of MAb 49 or MAb 77.

19. A method of treating a human patient that has a disease or condition selected from the group consisting of myocardial infarction, thrombosis, ischemic stroke, and pulmonary embolism, comprising:
   a) selecting a monoclonal antibody for an ability to specifically bind to a human α2-antiplasmin molecule at a binding site to convert the human α2-antiplasmin molecule from a serine protease inhibitor to a serine protease substrate,
   b) determining an effective amount of the monoclonal antibody for myocardial infarction, thrombosis, ischemic stroke, and pulmonary embolism by increasing the conversion of the α2-antiplasmin molecule from the serine protease inhibitor to the serine protease substrate in the patient, and
   c) administering to the patient an effective amount of a pharmaceutical composition comprising the effective amount of the selected monoclonal antibody.

20. The method of claim 19, wherein the serine protease is plasmin.

21. The method of claim 19, wherein the binding site comprises a serpin domain that does not include a reactive center loop of the α2-antiplasmin molecule.

22. The method of claim 19, wherein the binding site comprising the amino-terminus of α2-antiplasmin.

23. The method of claim 19, wherein the binding site is adjacent to the site at which α2-antiplasmin cross-links to fibrin.

24. The method of claim 23, wherein the binding site has an amino acid sequence of LGNQEPGGQTALKSPPGVCS (SEQ ID NO:1).

25. The method of claim 19, wherein the monoclonal antibody comprises Fv fragments of MAb 49 or MAb 77.

* * * * *

UNITED STATES PATENT AND TRADEMARK OFFICE
CERTIFICATE OF CORRECTION

| | | |
|---|---|---|
| PATENT NO. | : 9,834,614 B2 | Page 1 of 1 |
| APPLICATION NO. | : 14/872776 | |
| DATED | : December 5, 2017 | |
| INVENTOR(S) | : Guy L. Reed | |

It is certified that error appears in the above-identified patent and that said Letters Patent is hereby corrected as shown below:

In the Specification

Column 1, Lines 19-22, please replace the paragraph under the ACKNOWLEDGEMENT OF FEDERAL RESEARCH SUPPORT from "This invention was made, in part, with Government support under National Institutes of Health Grant HL-058496 to G.L.R. Accordingly, the United States Government has certain rights in this invention." to --This invention was made with government support under grant HL058496 awarded by the National Institutes of Health. The United States Government has certain rights in the invention.--

Signed and Sealed this
Thirty-first Day of December, 2024

Derrick Brent
*Acting Director of the United States Patent and Trademark Office*